United States Patent [19]
Knapp

[11] Patent Number: 5,365,343
[45] Date of Patent: Nov. 15, 1994

[54] LIGHT FLUX DETERMINATION OF PARTICLE CONTAMINATION

[76] Inventor: Julius Z. Knapp, 22 Foxwood Dr., Somerset, N.J. 08873

[21] Appl. No.: 96,619

[22] Filed: Jul. 23, 1993

[51] Int. Cl.$^5$ .............................................. G01N 21/90
[52] U.S. Cl. ..................................... 356/427; 356/240
[58] Field of Search ............... 356/427, 428, 237, 238, 356/240

[56] References Cited

U.S. PATENT DOCUMENTS

| | | |
|---|---|---|
| 3,627,423 | 12/1971 | Knapp et al. . |
| 3,765,533 | 10/1973 | Stephens et al. . |
| 3,900,266 | 8/1975 | Takahashi et al. . |
| 3,914,058 | 10/1975 | Knapp et al. . |
| 3,942,897 | 3/1976 | Takahashi et al. . |
| 3,966,332 | 6/1976 | Knapp et al. ..................... 356/240 X |
| 4,095,904 | 6/1978 | Klein . |
| 4,158,625 | 6/1979 | Takahashi et al. ................... 209/524 |
| 4,303,342 | 12/1981 | Takahashi et al. ................... 356/427 |
| 4,492,475 | 1/1985 | Takahashi et al. ................... 356/427 |
| 4,676,650 | 6/1987 | Bjorndal et al. ..................... 356/427 |

OTHER PUBLICATIONS

Knapp, J. Z. et al., "Generalized Methodology for Evaluation of Parenteral Inspection Procedure", *Bull. Parenter. Drug Assoc.*, 34:14 (1980).

Knapp, J. Z. et al., "Implementation and Automation of a Particulate Detection System for Parenteral Products", *J. Parenter, Drug Assoc.*, 34:369 (1980).

Knapp, J. Z. et al., "Automated Particulate Detection for Ampuls Using the Probabalistic Particulate Detection Model", *J. Parenter. Sci. Technol.*, 35:21 (1981).

Knapp, J. Z. et al., "Particulate Inspection of Parenteral Products: An Assessment", *J. Parenter. Sci. Technol.*, 35:176 (1981).

Knapp, J. Z. et al., "Particulate inspection of Parenteral Products: From Biophysics to Automation", *J. Parenter. Sci. Technol.*, 36:121 (1982).

Knapp, J. Z. et al., "Inventory and Measurement of Partricles in Sealed Sterile Containers", *J. Parenter. Sci. Technol.*, 37:170 (1983).

*Primary Examiner*—Vincent P. McCraw
*Attorney, Agent, or Firm*—Klauber & Jackson

[57] ABSTRACT

A method and device for the automated non-destructive single inspection of solutions in transparent containers for particle contamination, in injectable pharmaceutical solutions, with commercially viable acceptance percentages, while maintaining security within guidelines based on skilled human inspection. The containers are fully illuminated with forward scatter lighting with total light flux for detection of low contrast particles, with the size of the particles being evaluated by the maximum instantaneous increase of detector current as the particle moves through the detection zone. Simultaneously therewith, narrow detection volumes are back lighted with collimated light flux for detection of high contrast or dark particles, within the detection volume, by light extinction with a decrease of detector current from the normal non-particle illumination. The maximum pulsatile current decrease is used to determined the size of the particle. Separate illumination elements provide the forward scatter light and the back lighting, and separate, non-overlapping detector areas capture the separate increase and decrease of detector current. Either separate detectors with separate lenses are utilized for detection of the increase and decrease of detector current or mirrors are utilized to reflect the respective images through a single lens onto separated sections of a single detector element.

29 Claims, 5 Drawing Sheets

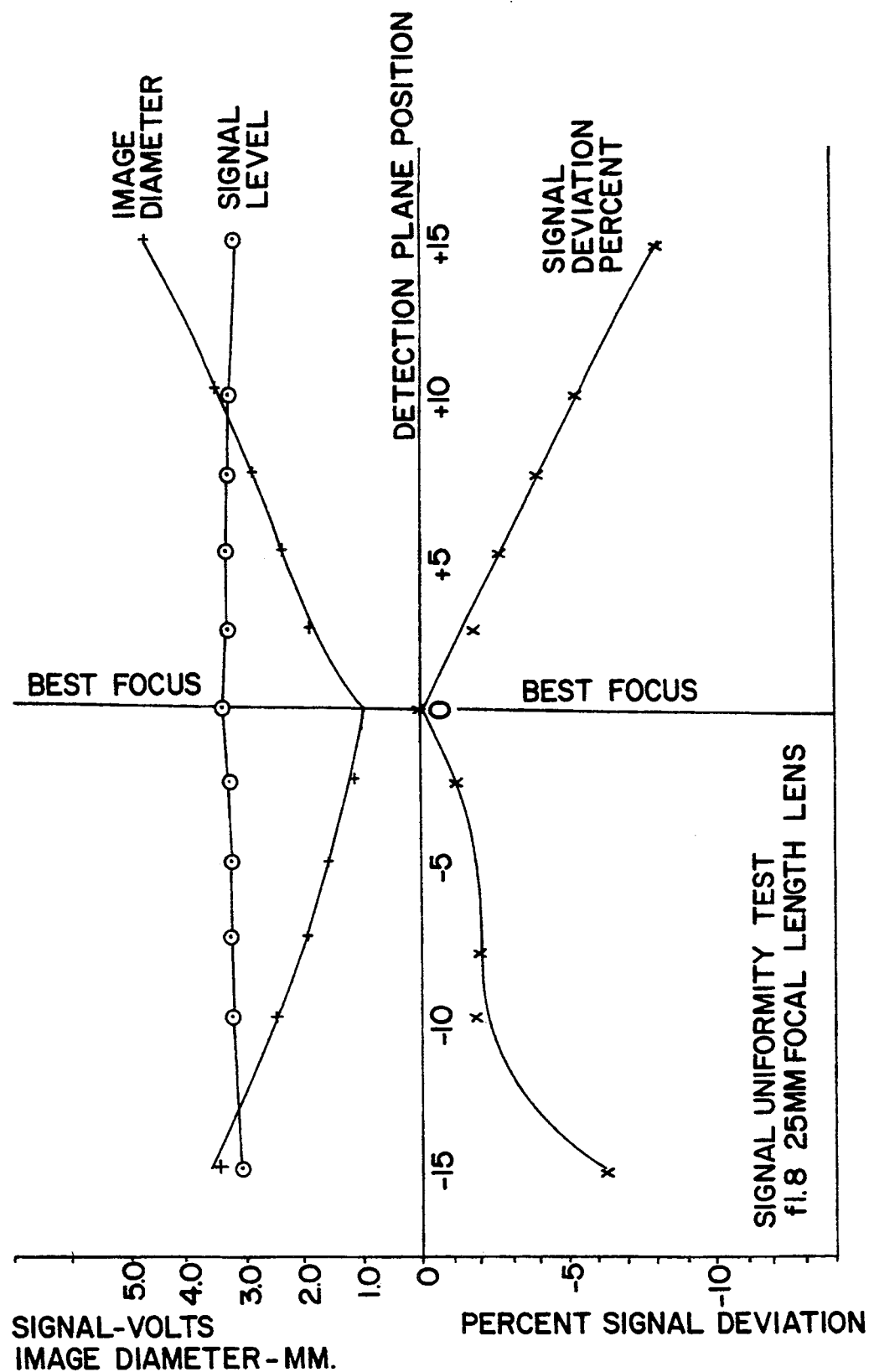

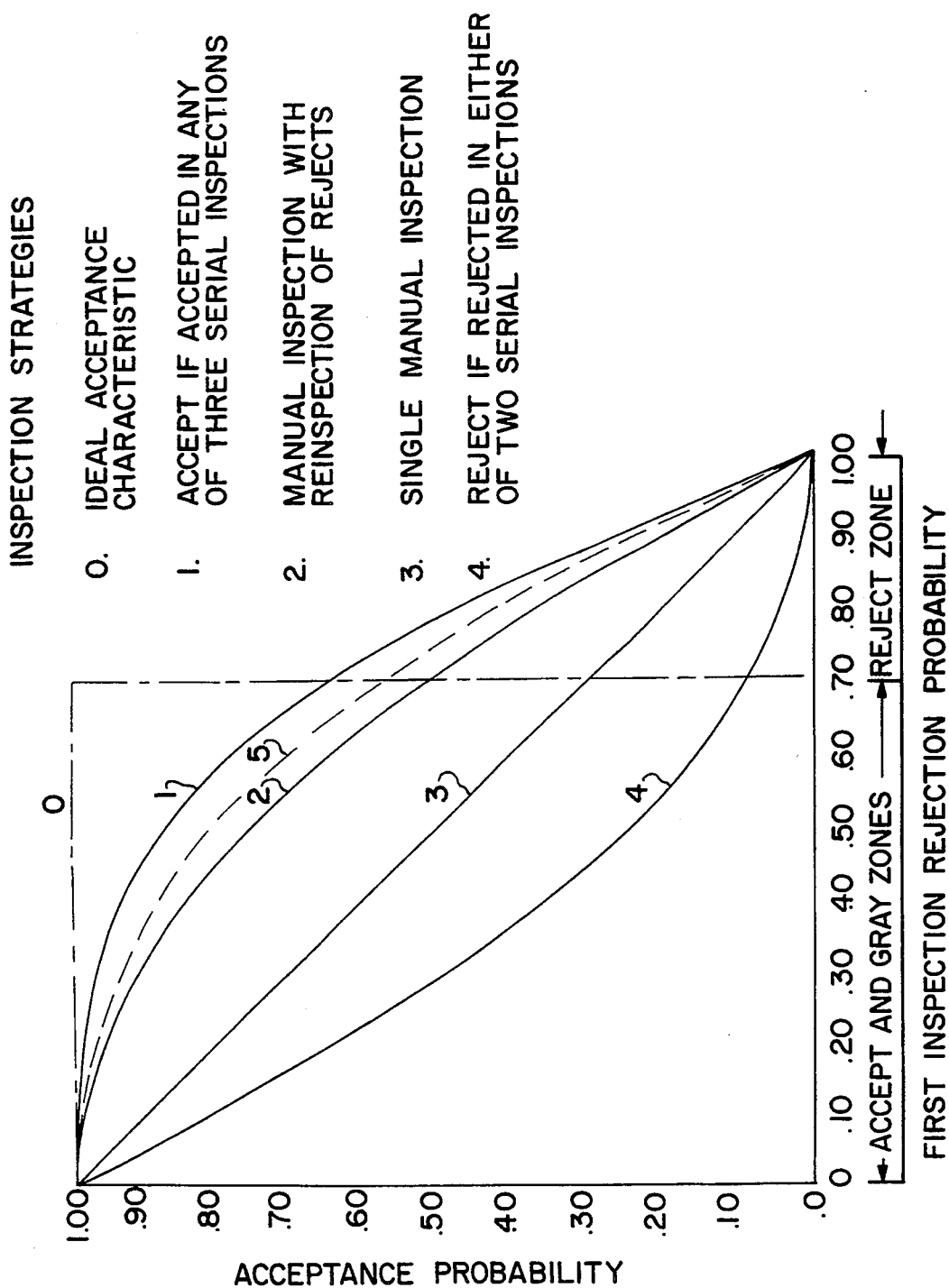

LIGHT FLUX DETERMINATION OF PARTICLE CONTAMINATION

FIELD OF THE INVENTION

This invention relates to automated non-destructive inspection of solutions in transparent containers for particle contamination and particularly to the determination of particle contamination in injectable pharmaceutical solutions.

BACKGROUND OF THE INVENTION

Injectable pharmaceutical solutions are unsuitable for use if particle contamination is visible in non-destructive visual inspection or the distribution of sub-visible particles exceed the number and distribution of the pharmacopeial quality standard in sampled destructive tests. Because of the nature of the use it is a requirement that, whenever possible, each container, having such solution, be subjected to visual quality control inspection and analysis to determine suitability. The pharmacopeial standard and basis for this test is that of a skilled human inspector, i.e. rejection on the basis of particles visible to the human eye. Human inspection is however costly, slow and variable, with efforts having been expended upon development of automated inspection systems.

For an automated particle contamination inspection system to be validated, its performance must be at least equivalent to that of the standard established by the skilled human inspector. In determining the basis for the skilled human standard, the range of inspected containers has been defined as encompassing three separate probability zones of container acceptability. Based upon the accepted quality definition, "bad" containers are those having a rejection probability equal to or greater than 70% in a single visual inspection (Reject Zone). "Good" containers are those rejected less than 30% in a single visual inspection (Accept Zone). Those containers having probabilities of rejection between 70 and 30% are categorized as being in a Gray Zone. Automated non-destructive inspection devices should provide an average rejection rate for all the containers, that human inspection identifies as being within the Reject Zone, and are matched by the device, within an acceptable confidence interval. In addition, for economic considerations, false rejection of Accept and Gray Zone containers should be minimal.

In real size terms, 100 $\mu$m particles are the smallest that can be detected by experienced inspectors, with unaided vision, 70% of the time; 50 $\mu$m particles are rarely detected; and 200 $\mu$m particles are always detected. As a result, automated inspection should be able to reliably, (i.e. with probability of rejection equal to or greater than 70%) reject particles of 100 $\mu$m and greater.

The evaluation of injectable products by visual inspection, where possible, and the determination that injectable products are "essentially free from particles that can be observed by visual inspection", mandate the visual or visual equivalent inspection as a prerequisite for product acceptance and sale.

At present, there is no automated inspection which delivers the required skilled human standard for inspection security and an acceptable false rejection rate in a single inspection. In order to achieve automated inspections comparable to those of human inspectors (without excessive rejections), it has therefore generally been necessary that containers be subjected to two or even three separate inspections. One common type of inspection is the "accept in two" strategy in which the containers accepted as good in the first inspection are sent to stock. The bad containers from a first inspection are re-inspected and if containers are then found to be good they are added to the accepted stock. An "accept in three" strategy adds a third inspection for the culling of additional acceptable stock, though with a reduction in security. A current widespread inspection strategy, used by Japanese and Italian inspection systems, involves a "reject in two" strategy in which a container is rejected if it fails to pass either of two serial inspections. The ability of a system to reject containers within the Reject Zone is defined as the Reject Zone Efficiency or RZE. Manual inspection peaks at about 90% RZE for a first inspection, with a slide to about 80% with a second ("accept in two") procedure. Reject Zone Efficiency, after the second inspection, must be matched for validation. RZE for a "reject in two" inspection usually ranges from 70–80%

In addition to the visual inspection, a destructive sampling procedure, for sub-visual particles, i.e., less than 50 $\mu$, is also employed for the evaluation of contaminating particles in these solutions. Marketed injectable solutions in the U.S.A. must contain fewer contaminating particles >10 $\mu$m and >25 $\mu$m than limits established by the U.S. Pharmacopoeia.

A commonly utilized form of automated non-destructive type of inspection, particularly in a sterile production line setting, involves the illumination of suspended particles, with detection of the particle images for a determination of particle size and number. Various procedures have evolved to minimize either uneconomical excessive rejection rates of potentially acceptable containers or undesired acceptance of rejectable containers with consequent degradation in quality. Nevertheless, a high degree of inaccuracy remains, with acceptance of containers which should be rejected and rejection of containers which should be accepted.

A common automated procedure, exemplified by U.S. Pat. Nos. 3,627,423 and 4,676,650; for non-destructive inspection, entails rapid rotation of the solution container about its own axis, with the container being suddenly stopped. Because of inertia, particles within the solution, continue in motion, in generally decaying circular spirals. The orbits and decay times are related to the size, weight and hydrodynamic characteristics of the individual particles and to the viscosity of the suspending solution. The moving particles are then illuminated for inspection and the image signals of the illuminated particle are detected and evaluated for size and number. The particle movement and illumination thereof enables the ready differentiation of the moving particles from static imperfections in the container material, usually of a non-optical grade of glass, from external dirt particles on the container, or printed information thereon. Another method for inducing particle movement or motion is inversion of the container during illumination and inspection. The post spin or inversion inspection can be accomplished with either a stationary container or one in continuous rotational translation, i.e., moving an assembly within a turret.

Errors are, however, inherent in the present common scanning methods which make it difficult to achieve more than about 80% rejectable container rejections, with the "reject in two" inspection, and 90% rejectable container rejections, with the "accept in three" inspections. Several major factors in prior art methods result in limitations of accuracy. In these methods, only a fraction of the particles in the container volume are effectively illuminated and imaged during a single inspection. The position of the particle at commencement of the inspection is random. To be detected, the particle must traverse the limited inspected volume. This required condition results from particle illumination and/or imaging being limited to particles in a small portion of the container volume. For the "reject in two" automated inspection, the inspected volume can be a rectangular volume approximately 1 mm thick, centered on the optical axis of the inspection system. For particle imaging systems, the shallow-depth inspected volume, using this inspection strategy, is centered generally on the optical axis of the container near the container wall. The signals from these particles are considered an optical signature which is compared to stored criteria to determine particle contamination of the entire solution.

The security of the inspection, however, can be no better than the proportion of the total container liquid volume examined in the inspection. It is therefore essential that substantially all of the container liquid volume be examined for particles. In the present art, the use of separate inspections does not effect this desirable full container inspection, due to the random portion of the particles at the start of each inspection. Instead it provides an improvement in probabilistic detection capability. However, the use of multiple inspections, with container rejections based upon rejection in any of the multiple sequential inspections, while increasing inspection security, reduces the acceptance rate of usable gray zone containers.

Physical limitations of the inspection devices for the inspection methods, and restrictions of inspection time, result in the limited inspection of only a portion of the liquid of the container volume. Methods relying upon the direct illumination of particles by light sources, e.g. perpendicularly directed at a plane through the container axis, wide or narrow width, collimated light, i.e., light extinction illumination, such as disclosed in U.S. Pat. No. 3,900,266, usually result in only a fraction of the particles passing through the scanned light beam paths during the inspection time, depending on initial particle position velocity, and the duration of the inspection period.

Even with illumination of the entire solution, by high intensity forward scattering light (light that is oriented outside the acceptance angle of the viewing lens to illuminate the entire solution), only a small portion of the solution is inspected at any instant in time. Particle imaging methods relying on a determination of the edges of the imaged particles are limited in accuracy by the focal length at which sharpness of focussed image can be obtained. For example, for an f1.0 lens with a focal length of 75 mm, at unity, object to image size ratio (permitting full resolution of the lens), the depth of acceptable image sharpness is approximately 0.2 mm. This can be increased to approximately 1.6 mm by reducing the lens aperture to f8.0. However, even the smallest containers range in size from 10–30 millimeters in diameter. As a result, even with full container illumination, only a very shallow portion of the solution, is sufficiently in focus for accurate inspection and particle size determinations based upon this type of particle imaging. In addition, such systems are susceptible to inherent errors caused by system vibration, which tends to limit accurate focussing.

For those systems employing some version of light extinction particle detection, the use of collimated light with an on-axis column array of photo detectors define a small volume particle detection zone. Typically the zone is 1 mm wide and includes the liquid height of the container.

In both types of detection systems, the proportion of the container volume inspected for particulate contamination at any instant in time is small. There is explicit dependence upon particle motion within the container to bring the particle through the detection zone for the inspection to be effective.

In particular designs, some high brightness areas are vignetted during the inspection period to accommodate the limited dynamic range of the detector employed. In some designs the container bottom is vignetted during the inspection period and in other designs, the meniscus portion of the container is vignetted either alone or with the container bottom. In both cases, the inspected volume of the container is reduced, thus reducing the security of the inspection.

In order to increase rejection probability of required rejects, two scans, with rejection in either one, can be utilized but with reduction in rate of overall production processing and a reduction of acceptable gray zone containers. With two or three scans it is also possible to use both forward scatter lighting and direct lighting (typically with an intensity from 0.001 to 0.01 that of the forward scatter beam intensity) to illuminate particles, susceptible to each, in separately illuminated scans, such as described in U.S. Pat. No. 4,492,475. Light colored particles reflect and scatter light toward the detector with a net increase in light energy collected, i.e., positive height pulses. Dark colored particles do not reflect light well but rather block off direct lighting which, with a resultant shadow and a decrease in energy toward the detector, result in reduced signal output, i.e., negative height pulses. The use of two sequential measurements with rejection, if rejected in either respect, is however, less effective than the combined use of both types of illumination in a single station.

Despite greater effectiveness, utilization of both types of lighting in a single scan, such as for example, disclosed in U.S. Pat. No. 4,676,650, introduces algebraic errors with reduction in inspection efficiency. These errors result from illumination of particles, which are susceptible to illumination and detection by both types of lighting, i.e., positive energy imaging from forward scattering light reflections and negative energy from shadowing of direct lighting.

SUMMARY OF THE INVENTION

The present invention comprises a method and a device for automated non-destructive inspection of injectable pharmaceutical solutions, in transparent containers, for particle contamination. Specifically, the method comprises the steps of initially moving the solution container, whereby particles, contained therein, are placed in motion. The solution in the container, is then illuminated, while the particles are in motion, with forward scatter lighting, which lighting is detected by a first detector element such as a photo detector. The photo detector, as a result of the impingement of light thereon, emits a current signal which is directed to a first current detector for subsequent signal processing. With particle contamination, there is an instantaneous increase of the normal current flowing from the photo detector to the current detector, caused by reflection of light by individual particles, detected by the photo detector, with the increase of current being proportional to the size of the individual particles.

At the same time that the solution is being subjected to forward scatter lighting, a volume of the solution is also subjected to back lighting with collimated light, which is detected by a second light detector element, such as another photo detector or a separated portion of the first photo detector. As with the first photo detector, the second photo detector, as a result of the impingement of light thereon, emits a current signal which is directed to a second current detector. With particle contamination, there is light extinction caused by individual particles passing through the volume, with an instantaneous decrease of current from the second photo detector relative to the normal illumination in the volume. The value of the instantaneous decrease of current is proportional to the size of the individual particles.

The absolute values of the detected increases and decreases of current, related to the particles sizes, from the separated light and current detectors are summed, without overlapping algebraic errors, into a reliable optical signature of particle contaminants in the container solution. Containers having optical signatures falling within pre-determined acceptable optical signature ranges are accepted with an exceptionally high degree of certainty.

The device of the present invention for automated non-destructive inspection of injectable pharmaceutical solutions, in transparent containers, for particle contamination, comprises the means for moving the solution container, whereby particles, contained therein, are placed in motion. The device further comprises means for fully illuminating the solution in the container, while the particles are in motion, with forward scatter lighting; and means for back lighting a volume of the solution in the container with collimated light, during the period when the solution in the container is fully illuminated with forward scatter lighting. The device includes separate light detectors, such as photo detectors, for detecting the forward scatter lighting and the back lighting, and which photo detectors emit separate current signals to separate current detectors. The device further includes computer means for summing the absolute values of the detected increases and decreases of current into an optical signature of particle contaminants in the container solution, with comparison means, comparing the optical signal to a pre-determined optical signature range for determining acceptance of the container solution.

It is an object of the present invention to provide a method and device which enables the accurate complete particle contaminant detection scanning of a liquid solution.

It is a further object of the present invention to provide said method and device with the capability of using both forward scattering light and back illumination in a single inspection period without algebraic errors in detection, thus improving the discrimination of the acceptance decision by improving particle detectability and sizing.

It is a still further object of the present invention to provide a method and device for the inspection of the entire solution for particle contamination with relative independence from the need for a focussed image, with comparison to a stored optical signature to determine acceptability rather than limited inspection of only a portion of the solution by either focussed particle imaging or light extinction imaging.

These and further objects, features and advantages of the present invention will become more apparent from the following discussion and the drawings in which:

SHORT DESCRIPTION OF THE DRAWINGS

FIG. 1c is a comparative graph showing deviations in the size of focussed image, typical of the inspection station shown in FIG. 1 with lighting sources as shown in FIGS. 1a and 1b, relative to that of the present invention.

FIG. 4 is a comparative graph of detection curves for different methods including that of the present invention relative to ideal inspection and rejection.

DETAILED DESCRIPTION OF THE INVENTION

Figure 1:
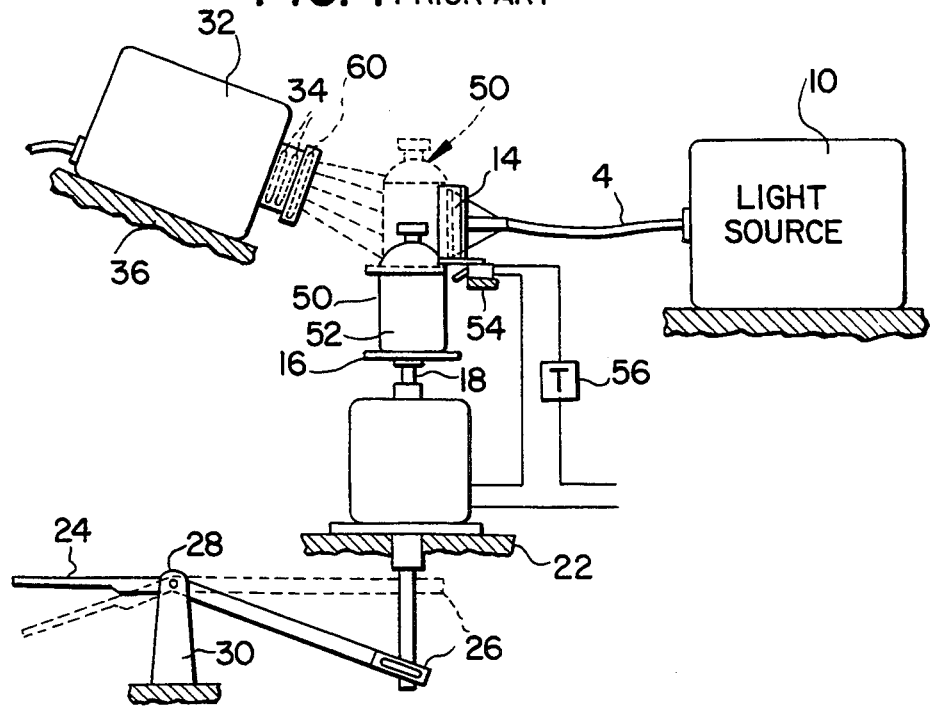
FIG. 1 is a representation of a prior art inspection station showing the portions of a container being inspected in a single illumination scan.

Generally the present invention comprises a method, and device for effecting such method, for efficient single inspection period illumination inspection of particulate contaminants in a solution. The method is most applicable to low contamination rate injectable pharmaceutical solutions contained within transparent containers. As with currently utilized and other prior art inspection methods, the container and solution are placed in motion, such as by being rapidly rotated and stopped, whereby particles contained therein are placed in motion and remain in motion during subsequent illumination and inspection. The entire solution is then illuminated by a forward light scattering source, and simultaneously therewith a portion of the solution is illuminated by one and preferably at least a pair of narrow beam collimated light sources. During illumination, the maximum of the total light flux of light colored and dark particles signals is evaluated.

In accordance with the present invention, the illuminated imaging of the particles is relatively independent of sharply focussed imaging with defocussed positive and negative energy pulse heights, rather than sharply focussed images of the particles, with determination of the edges of the imaged particle, as obtained with current inspection methods. The defocussed positive energy pulse heights of substantially all the particles within the solution are effectively inspected, by determination of the variation in total light flux captured by a uniform image light detector or collector such as a photo transducer, or photo transducer array, proportioned to capture the maximally defocussed image of the largest particle for which the inspection system is designed. The image light receptor or collector emits corresponding energy pulse signals to an energy detector for further processing.

Since particle motion is essentially horizontal in the after spin inspection period, the photo detector employed comprises multiple sensor blocks arranged in horizontal rows and vertical columns. The column array provides redundant particle signals for greater accuracy in detection. The vertical columns are divided into detection blocks which permit a phased inspection commencing at the container bottom, to inspect the rapidly damped movement of heavy particle signals. The inspected container height is increased at a rate determined by the stabilization of the meniscus to provide improvement of particle signal to noise ratio. The area of the sensor blocks is proportioned to accommodate the maximally defocussed image of the largest particle to be determined, as well as sufficient residence time to ensure measurement accuracy. It is preferred that a uniform photo detector surface be utilized for image processing as opposed to the commonly utilized fiber optic image dissectors or arrays of photo detector elements such as in CCD arrays, in order to eliminate signal modulation resulting from non-transmission of particle signals by the separation of photo signal conversion or transmission areas.

The beam width of the direct lighting sources is preferably in a range from 5 to 25% of the diameter of the container being inspected. Beam heights for both the direct and forward scattering light sources are varied during the inspection period with a range of beam height from 20 to 95% of the minimum liquid meniscus height being preferred.

The light paths of both the forward scatter lighting and direct lighting are arranged to provide bi-directional energy pulse height imaging of the illuminated particles on separate areas of totally separated light detectors or on separated designated areas of a single photo detector with a continuous substrate. The direct or back lighting source is positioned to produce an image outside of that produced by the forward scatter illumination to avoid the subtractive interferences of the present art. Alternatively, mirrors or prisms can be utilized to direct beamed energy through the acceptance angle of a single lens for separated imaging on the image collector plane. The light paths of both the forward scatter lighting and direct lighting can be imaged through a single lens, provided that there is no overlapping of imaging on the photo-transducer. Alternatively, separate lenses can be utilized for the imaging of the forward scatter light illumination and the direct light illumination. With the separation of image detection, the signals can be separately detected by separate detector elements for processing and calibration and combination, without the algebraic errors of the prior art. In addition, because of the separation of illumination signals, the relative intensity of the direct illumination beams to the forward scatter illumination can range from 0.10 to about 1.0 without substantial interference of signals.

With larger container diameters, longer focal length lenses can be effectively utilized for complete container inspection, since the particle imaging of the present invention is not dependent upon precisely focussed particles. Instead, the imaging lens (or lenses) is employed at its greatest aperture as an energy collector, with an approximate ten fold increase of particle signal due to improved energy collection efficiency.

Though a single axially directed beam can be utilized in accordance with the present invention, it is preferred that multiple beams be utilized to minimize the maximum orbital travel required by large or dark particles to enter a detection zone. The use of such multiple axially directed beams reduces the time required for inspection by reducing the orbital transverse time for a particle to enter a detection volume.

DETAILED DESCRIPTION OF THE DRAWINGS

Figure 1A:
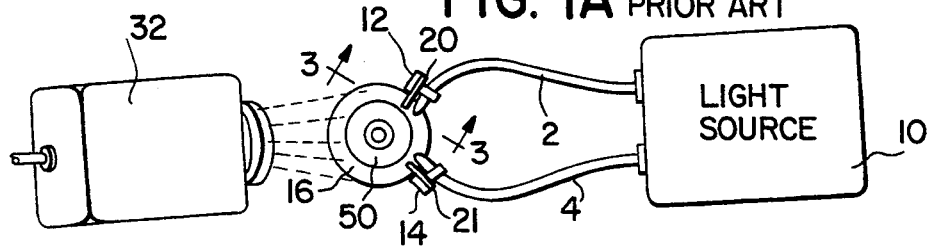
FIGS. 1a and 1b are diagrammatic representations of prior art forward scatter light sources; and combination direct light and forward scatter light sources respectively, as used with the inspection station of FIG. 1.
Figure 1B:
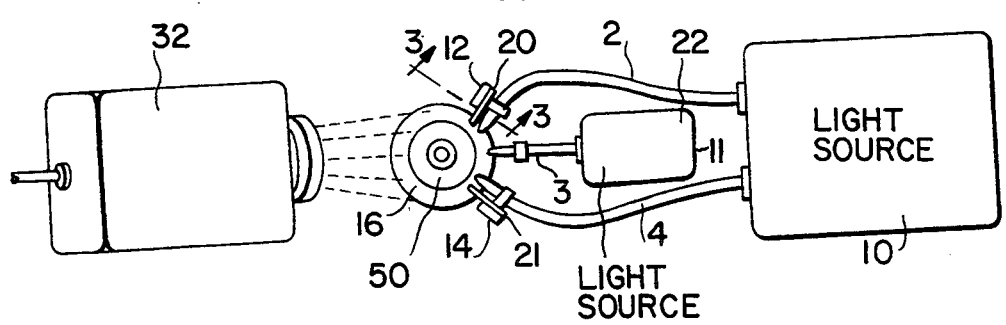

With specific reference to the drawings, in prior art FIGS. 1, 1a and 1b, pharmaceutical vial 50 is illuminated after being rotated, stopped, and elevated into illumination position (shown in dotted lines) by a light source 10. In FIG. 1a, the light source comprises angled collimated optical fiber light sources 20 and 21 which provide lighting for forward scatter light detection of particles within vial 50, by camera 32, though lens elements 34. Particle detection is accordingly limited to those particles which traverse the shallow focussed zone during the illumination time interval.

In FIG. 1b, there is an additional light source 22 which provides back or direct illumination through the vial 50 for a detection of particles by light extinction as well, also through lens element 34. However, as described above, with respect to U.S. Pat. No. 4,676,650, there are algebraic errors introduced by particles which are susceptible to both types of lighting. Cameras 32 in the prior art, detect particle image by light reflection and extinction in the same detection area. Other detectors, such as the photo-transducer in US Pat. No. 4,087,184, are utilized with a single lens element which similarly results in detection of the particle image in the same detection area.

In prior art particle illumination inspection devices, detection is of the focussed particle image with a methodology which relies on the determination of the edges of an imaged particle. However, as is apparent from the graph of FIG. 1c, the sharpness of an image is limited by the focal depth in which sharp images can be obtained. The depth of focus, even with a small aperture lens, e.g. f8, has a depth of focus of about 1.6 mm, only a fraction of the volume of containers which generally range from 10 to 30 mm in diameter.

With reference to FIG. 1c, showing experimental data with a 75 mm f1.8 lens using a 1 mm circular target, a ±15 mm focal depth from the plane of best focus results in a −8.1% light flux measurement error at an image plane 15 mm beyond the position of best focus in the measurement of the circular target. At an image plane position 15 mm short of the best focus plane, the light flux measurement error was −6.3%. The diameter of the target image therefore varied by a maximum of 470% in the 30 mm depth of focus zone of a typical container for a worst case variation of −8.1% with peak flux signal.

In accordance with the present invention, such errors are minimized by determination of the variation in total light flux captured by a collector such as a photo transducer or CCD areas, proportioned to capture the maximum defocussed image of the largest particle for which the inspection system is designed. This is depicted as signal level variation shown in FIG. 1c. In effect, rather than measuring focussed images with concomitant deviations, measurement is made of peak flux signals caused by particle illumination (positive values) and by particle light extinction (negative values) with an absolute value summation for total detection values. This also permits greater accuracy in detection of sub-visible particles in the 10μ to 25μ particle range. Furthermore, the accuracy of collection and energy detection is not affected by system vibration, inherent in container-spin systems, which detrimentally affect particle image focussing in such prior art detection systems.

Figure 2:
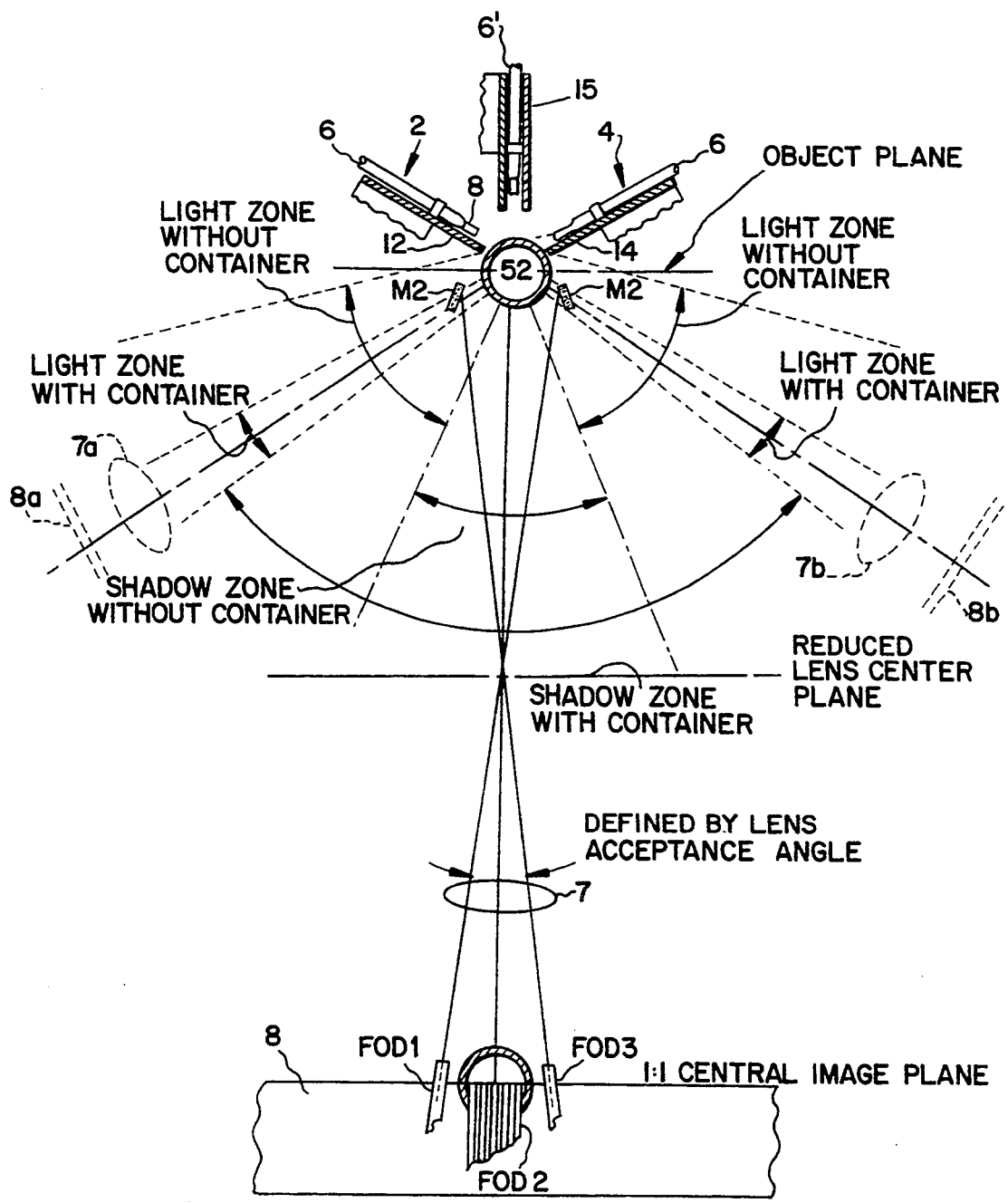
FIG. 2 is a top schematic view of an inspection station of the present invention with non-overlapping portions of forward scattered lighting and direct illumination for complete particle inspection.

In order to avoid overlapping detection errors, engendered by particles which are responsive to both illumination and extinction signals, there is a specific separation of the defocussed image collectors or detectors for each of the signals. As shown in FIG. 2, mirrors M1 and M2 separate the direct illumination and light extinction signals from light sources 6 away from that of the forward scatter light source 6', through the acceptance angle of single lens 7, to provide separated images FOD 1 and FOD 3, on separate portions 8' and 8" of photo detector 8, which are distinguished from larger scatter light image FOD 2. As shown, all the light is redirected to the single lens 7 prior to detection. However, the use of mirrors can be dispensed with, as shown in dotted lines, by utilizing separate lenses 7a and 7b for each of the light sources, with separate defocussed image and photo detectors 8a and 8b. The photo detectors 8a and 8b and the separate portions 8' and 8" of photo detector 8 emit current signals to current detectors 9a and 9b, which are linked together by summation means for integration of the signals into an optical signature which is thereafter used for comparison to acceptable optical signatures in determining acceptability of the container.

For effective signal detection in accordance with the present invention, the intensity of the quiescent light received in the image plane should be at least >5 greater for the direct light sources 6 over that of the forward scatter light source 6', and more desirably between 10 and 50 times.

In FIG. 2, FOD 1 and FOD 3 are the two side light direct beam fiber optic image dissector conduits bringing the side beams to photo detector 8. As depicted, FOD 1 and FOD 3 are closer to the lens 7 than the central image dissector. This difference in location is required to bring the central image plane for the two back light sources 6 into optimum focus as compensation for the increase from the central object plane to the imaging lens from 1:1. FOD 2 is a five section fiber optic image dissector, with the center section being the image conduit for the central direct light beam, and the two pairs to either side of the central conduit being the forward scatter light beam conduits bringing the forward scatter light signals to the appropriate detectors. Though a fiber optic image dissector is shown, in order to obtain economic advantages, direct photo detector imaging is technically superior.

Figure 3:
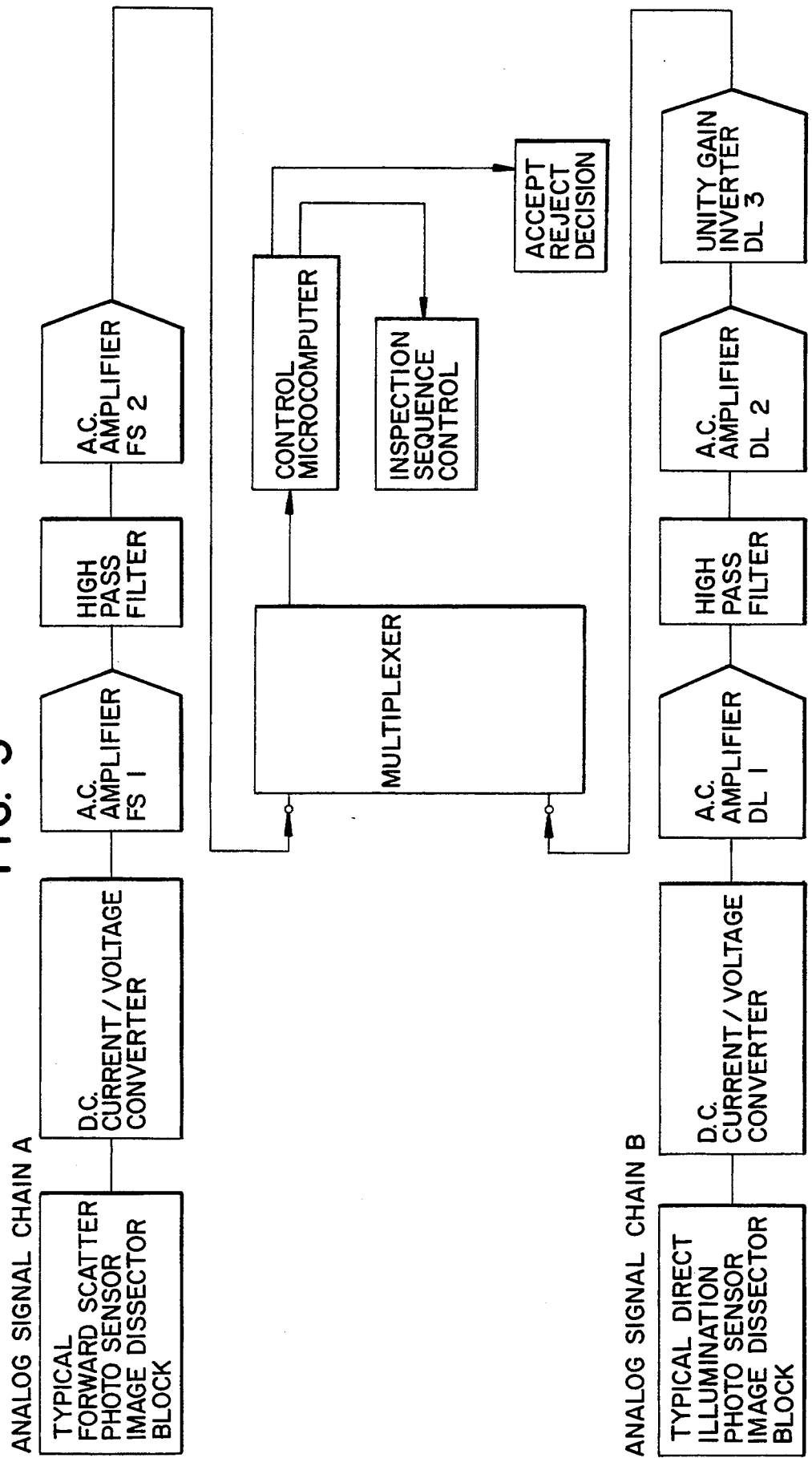
FIG. 3 is a sequential operation flow chart showing the separate and combined computerized processing of analog signals from forward scattered lighting and direct illumination of a solution.

The flow chart shown in FIG. 3, depicts the processing of the separated forward scatter photo sensor image dissector block (FOD 2) and the direct illumination photo sensor image dissector blocks (FOD 1 and FOD 3), with conversion from the analog D.C. signal to A.C. with signal amplification, noise filtering, secondary amplification, multiplexing, control by a micro-computer, with pre-programmed accept/reject decision parameters, and inspection sequence control. The separation of signal paths facilitates the use of independent amplification levels for both lighting means, thus making possible single accept/reject decision levels.

As shown in FIG. 4, the method of the present invention is compared to the ideal acceptance characteristic and the various manual and automated strategies. The method of the present invention which utilizes a single inspection, shown in curve 5, is at least comparable to that of the manual inspection with reinspection of rejects (curve 2) and approaches that of the ideal acceptance inspection.

It is understood that the above description, drawings and examples are merely illustrative of the present invention and that changes in type of components, number, configuration, and relative placement of the light sources, lenses, mirrors, detectors and the like are possible without deviating from the scope of the present invention as defined in the following claims. It is also understood that although a single inspection system is described herein, in cases where lower rejection rates are essential, a reinspection of rejects can be used without departing from the scope of the present invention.

What is claimed is:

1. A method for automated non-destructive inspection of injectable pharmaceutical solutions, in transparent containers, for particle contamination, said method comprising the steps of:
   a. moving the solution container, whereby particles, contained therein, are placed in motion;
   b. fully illuminating the solution in the container, while the particles are in motion, with forward scatter lighting; wherein there is an instantaneous increase of the normal current flowing from a first light detector element, which detects the forward scatter lighting, caused by reflection of light by individual particles; with said instantaneous increase of current being proportional to the size of the individual particles;
   c. directing said increase of current to first current detector means;
   d. back lighting a volume of the solution in the container with collimated light, during the period when the solution in the container is fully illuminated with forward scatter lighting, wherein there is light extinction caused by individual particles passing through said volume, with an instantaneous decrease of current from a second light detector element, which detects said collimated light, from normal non-particle illumination in said volume, and wherein said instantaneous decrease of current is proportional to the size of the individual particles;
   e. directing said decrease of current to second current detector means;
   f. summing the absolute values of the detected increases and decreases of current into an optical signature of particle contaminants in the container solution; and
   g. accepting containers having optical signatures falling within pre-determined acceptable optical signature ranges.

2. The method for automated non-destructive inspection according to claim 1, wherein intensity of light received by the respective detector elements is at least five times greater for the back lighting than that of the forward scatter lighting.

3. The method for automated non-destructive inspection according to claim 2, wherein intensity of light received by the respective detector elements is between 10 and 50 times greater for the back lighting than that of the forward scatter lighting.

4. The method for automated non-destructive inspection according to claim 1, wherein said particles are placed in motion by rapidly rotating the solution container, with the container being suddenly stopped, wherein particles within the solution, continue in motion, and wherein said particles are in motion when illuminated by said forward scatter lighting and back lighting.

5. The method for automated non-destructive inspection according to claim 1, wherein said light reflection and light extinction pass through an acceptance angle of a single lens to said first and second detector elements.

6. The method for automated non-destructive inspection according to claim 5, wherein said light extinction, with subsequent decrease in current, is directed to the lens by reflective mirror means.

7. The method for automated non-destructive inspection according to claim 1, wherein said back lighting of a volume of the solution in the container with collimated light, is effected by at least two separated light sources.

8. The method for automated non-destructive inspection according to claim 7, wherein light extinction of collimated light from each of the at least two separated light sources, with subsequent decrease in current, is directed though a separate lens respectively to separate second detector elements.

9. The method for automated non-destructive inspection according to claim 8, wherein said separate detector elements comprise uniform image receptors.

10. The method for automated non-destructive inspection according to claim 9, wherein said uniform image receptors comprise photo detectors.

11. The method for automated non-destructive inspection according to claim 9, wherein said uniform image receptors comprise a photo detector array.

12. The method for automated non-destructive inspection according to claim 9, wherein said uniform image receptors comprise a CCD array.

13. The method for automated non-destructive inspection of claim 9, wherein said uniform image receptors are proportioned to capture, with said increase and decrease in current, a defocussed image of the largest particle to be detected.

14. The method for automated non-destructive testing according to claim 1, wherein the detected increases and decreases of current are separately directed from said first and second detection means to computer means which effects said summing of the absolute values of the detected increases and decreases of current into an optical signature of particle contaminants in the container solution; and wherein said computer means compares the optical signature of particle contaminants in the container solution to the pre-determined acceptable optical signature, stored in memory of said computer means, to provide said decision in accepting the container solution.

15. The method for automated non-destructive inspection according to claim 11, wherein efficiency of said decision is in excess of 90% with a single inspection.

16. The method for automated non-destructive inspection according to claim 1, wherein said container has a diameter and said collimated light has a beam width, wherein the beam width of the collimated light is in a range from 5 to 25% of the diameter of the container being inspected.

17. The method for automated non-destructive inspection according to claim 1, wherein said solution in the container has a meniscus caused by said motion and a meniscus height measured from the bottom of the container; wherein the back lighting and the forward scatter lighting have beam heights respectively, wherein each of said beam heights is varied during the inspection period within a range of from 20 to 95% of the minimum height of the meniscus.

18. A device for automated non-destructive inspection of injectable pharmaceutical solutions, in transparent containers, for particle contamination, said device comprising:
   a. means for moving the solution container whereby particles, contained therein, are placed in motion;
   b. means for fully illuminating the solution in the container, while the particles are in motion, with forward scatter lighting; wherein there is an instantaneous increase from the normal current flowing from a first light detector element, which detects the forward scatter lighting, caused by reflection of light by individual particles; with said instantaneous increase of current being proportional to the size of the individual particles;
   c. first current detector means for detecting said instantaneous increase of current;
   d. means for back lighting a volume of the solution in the container with collimated light, during the period when the solution in the container is fully illuminated with forward scatter lighting, wherein there is light extinction caused by individual particles passing through said volume, with an instantaneous decrease of current from the normal current flowing from a second light detector element, which detects the back lighting and extinction thereof, and wherein said instantaneous decrease of current is proportional to the size of the individual particles which cause said light extinction;
   f. second current detector means for detecting said decrease of current;
   g. means for summing the absolute values of the detected increases and decreases of current into an optical signature of particle contaminants in the container solution; and
   h. comparison means for comparing the optical signal to a pre-determined optical signature range for determining acceptance of the container solution.

19. The device according to claim 18, wherein said means for moving the solution container comprise means for placing the solution container in motion by rapid rotation thereof, whereby with the container being suddenly stopped, particles within the solution, continue in motion.

20. The device according to claim 18, wherein said device comprises a single lens and wherein said light reflection and light, subject to said light extinction, pass through an acceptance angle of the single lens to said first and second detector elements.

21. The device according to claim 20, wherein device comprises reflective mirror means and wherein said light, subject to light extinction, is directed to the lens by reflective mirror means.

22. The device according to claim 18, wherein said means for back lighting of a volume of the solution in the container with collimated light, comprises at least two separated light sources.

23. The device according to claim 22, wherein said device comprises a number of lenses equal to that of the at least two separated light sources wherein light, subject to the extinction of collimated light from each of the at least two separated light sources, is directed though a separate lens respectively to separate detector elements.

24. The device according to claim 18, wherein said separate detector elements comprise uniform image receptors.

25. The device according to claim 24, wherein said uniform image receptors comprise photo detectors.

26. The device according to claim 24, wherein said uniform image receptors comprise a photo detector array.

27. The device according to claim 24, wherein said uniform image receptors comprise a CCD array.

28. The device according to claim 24, wherein said uniform image receptors are proportioned to capture, with said increase and decrease in current, a defocussed image of the largest particle to be detected.

29. The device according to claim 18 wherein said device comprises computer means, wherein the detected increases and decreases of current are separately directed from said first and second detection means to computer means which effects said summing of the absolute values of the detected increases and decreases of current into an optical signature of particle contaminants in the container solution; and wherein said computer means compares the optical signature of particle contaminants in the container solution to the pre-determined acceptable optical signature, stored in memory of said computer means, to provide said decision in accepting the container solution.

* * * * *